United States Patent [19]

Johnson

[11] Patent Number: 5,126,123
[45] Date of Patent: Jun. 30, 1992

[54] AEROSOL DRUG FORMULATIONS

[75] Inventor: Keith A. Johnson, Holmes Beach, Fla.

[73] Assignee: Glaxo, Inc., Research Triangle Park, N.C.

[21] Appl. No.: 649,405

[22] Filed: Feb. 1, 1991

Related U.S. Application Data

[63] Continuation-in-part of Ser. No. 545,437, Jun. 28, 1990, abandoned.

[51] Int. Cl.⁵ .................................................. A61L 9/04
[52] U.S. Cl. ......................................... 424/45; 424/43; 424/44; 424/46
[58] Field of Search ........................ 424/45, 43, 44, 46

[56] References Cited

FOREIGN PATENT DOCUMENTS 0372777 6/1990 European Pat. Off. .
WO91/11173 8/1991 PCT Int'l Appl. .
WO91/14422 10/1991 PCT Int'l Appl. .

OTHER PUBLICATIONS

Dalby, Byron, Shepard and Papadopoulas, CFC Propellant Substitutions P-134a as a potential replacement for P-12 in MDI's, 1990.

*Primary Examiner*—Thurman K. Page
*Assistant Examiner*—Louis A. Piccone
*Attorney, Agent, or Firm*—Charles T. Joyner

[57] ABSTRACT

This invention relates to aerosol inhalation drug formulations comprising one or more drugs and one or more soluble surfactants in propellant 134a.

21 Claims, No Drawings

AEROSOL DRUG FORMULATIONS

This application is a continuation-in-part of application Ser. No. 07/545,437, filed Jun. 28, 1990, now abandoned. This invention relates to aerosol inhalation drug formulations comprising one or more drugs and one or more soluble surfactants in propellant 134a.

BACKGROUND OF THE INVENTION

Drugs for treating respiratory and nasal disorders are frequently administered in aerosol formulations through the mouth or nose. Peter Byron, Respiratory Drug Delivery, CRC Press, Boca Raton, FL 1990, provides a background for this form of therapy. (As used hereinafter the terms "aerosol drug formulation" and "inhalation drug formulation" are synonymous and refer to one or more physiologically active chemical compounds in combination with excipients such as surface-active agents, "surfactants" and propellants.)

One widely used method for dispensing such an aerosol drug formulation involves making a suspension formulation of the drug as a finely divided powder in a liquefied gas known as a propellant. The suspension is stored in a sealed container capable of withstanding the pressure required to maintain the propellant as a liquid. The suspension is dispensed by activation of a dose metering valve affixed to the container. A metering valve may be designed to consistently release a fixed, predetermined amount of the drug formulation upon each activation. As the suspension is forced from the container through the dose metering valve by the high vapor pressure of the propellant, the propellant rapidly vaporizes leaving a fast moving cloud of very fine particles of the drug formulation. This cloud is usually directed into the body of the patient by a channeling device, e.g., a cylinder like or cone like passage, with one of its ends attached to the outlet of the pressurized container, and the other end inserted in the mouth or nose of the patient. Concurrently with the activation of the aerosol dose metering valve, the patient inhales the drug formulation particles into the lungs or nasal cavity. Systems for dispensing drugs in this way are known as "metered dose inhalers (MDI's)." [Ibid Byron, Pages 167–207.]

Many materials, including drug formulations, have a tendency to aggregate (also referred to as "flocculate" or "clump-up") when stored as fine particles having dimensions of a few microns in a suspension. For an aerosol delivery system to work properly the particle size should generally not exceed about five microns. As the particle size exceeds five microns, it becomes increasing difficult to maintain an efficacious aerosol dose with a predicable dispersion pattern upon activation of the metering valve. Further, the suspension should be uniform, that is, substantially free from large aggregates of the drug particle and be substantially homogenous throughout the container.

To minimize or prevent the problem of aggregation of fine particles, compounds known as surface active agents, or surfactants, are used to coat the surfaces of the fine particles and assist in wetting the particles with an aerosol propellant. The use of surfactants in this way to maintain substantially uniform suspensions is said to "stabilize" the suspensions. An ideal surfactant should have a relative high affinity for the suspended drug formulation and be chemically and physically compatible with the propellant as well as the drug formulation.

If it does not have these properties, the surfactant can possibly destabilize the suspension. Additionally, it must be essentially nontoxic.

For several years the chlorofluorocarbons (CFC's), for example, trichloromonofluoromethane, dichlorotetrafluoroethane and dichlorodifluoromethane, also known as "propellant 11" or "P 11", "propellant 114 or "P 114" and "propellant 12" or "P 12", respectively, have gained widespread acceptance as the propellants of choice for inhalation drug formulations. They are nonflammable, have low toxicity and reactivity, are compatible with many drug formulations and have the requisite physical attributes. See John Sciarra and Anthony Cutie, Theory and Practice of Industrial Pharmacy, Pages 589-619, Lea and Febiger, Philadelphia, 1986. However, in the past few years CFC's have been shown to cause depletion of the ozone layer of the atmosphere, a serious environmental problem. Scientists and governmental officials around the world have called for a phase-out of the use of CFC's. Some countries, e.g., Sweden, have completely banned the use of CFC's for aerosol products, while other counties have levied substantial taxes on them to encourage the use of other, environmentally safer propellants. See Dalby, et al., Pharmaceutical Technology, Mar. 26, 1990.

In recent years a nonchlorinated propellant chemically identified as 1,1,1,2-tetrafluoroethane also known as "propellant 134a" or "P 134a" has been promoted by major chemical manufacturers, notably DuPont and ICI, as an environmentally acceptable alternative to CFC propellants. Propellant 134a has physical properties comparable with P 12. Although like P 12 it is nonflammable and has a relatively low potential for interaction with a wide variety of products normally sold in aerosol form, its other chemical and solvent properties are different from P 12. For example P 134a is much less stable chemically than P 12 according to Dalby, et al. (see above).

Thiel in U.S. Pat. No. 4,357,789 teaches the use of propellan insoluble perfluorinated surface-active dispersing agents in CFC and perfluorinated propellants although P 134a is not specifically mentioned. These agents include perfluorinated sulfonamide alcohol phosphate esters and their salts, perfluorinated alkyl sulfonamide alkylene quaternary ammonium salts and perfluorinated alcohol phosphate esters and their salts. Thiel teaches that surfactants must insoluble in the propellant. Further, he teaches that the drug must be coated with the surfactant in an organic solvent dried, then added to the propellant mixture.

DESCRIPTION OF THE INVENTION

It has now been found that P 134a-soluble surfactants, especially soluble perfluorinated surfactants, effectively improve the stability of micronized inhalation drug suspensions in P 134a. (As used herein the terms "perfluorinated" and "perfluoro" mean that for at lease one alkyl group essentially all of the hydrogens are substituted with fluorine.) Accordingly, when a micronized drug, i.e., a drug having an average particle size of about 5 microns or below and a maximum particle size of less than about 10 microns, and a P 134a soluble surfactant are placed in P 134a in a pressurized container, there is considerably less tendency for the drug particles to aggregate and separate from the suspension than the drug formulation without such surfactant or with a P 134a hydrocarbon surfactant commonly used with a CFC propellant. Thus it is now possible with the present invention to prepare aerosol formulations of inhalation drugs with P 134a which have sufficient stability for the purposes of this invention to deliver the active drug in the desired way as presently marketed MDI's, but without the environmental problems associated with CFC's. As used herein the term "sufficient stability" means that the aerosol drug formulation remains as a suspension after shaking at least long enough to allow activation of MDI and administration by the patient. The time between shaking and administration is typically about 10 sec. and generally for the formulations of this invention the period of stability is at least about 30 sec.

An aspect of this invention is the use of one or more P 134a soluble surfactants to stabilize an inhalation drug in P 134a. A second aspect is an aerosol inhalation drug formulation comprising a physiologically effective amount of a micronized inhalation drug and one or more P 134a soluble surfactants in suspension in P 134a.

In a preferred aspect the invention provides an aerosol drug formulation comprising a physiologically effective amount of micronized inhalation drug and one or more P134a soluble surfactants in suspension in P134a which formulation is substantially free of P134a insoluble surfactant.

In a further or alternative aspect the invention provides an aerosol drug formulation comprising a particulate drug and one or more P134a soluble surfactants in suspension in P134a, which formulation is substantially free of drug which has been coated with surfactant prior to addition to the propellant mixture.

The drugs useful in this invention include those drug adaptable to inhalation administration, for example, antiallergic, respiratory (e.g. antiasthmatic and bronchodilating), antibiotic, antiinflammatory, antifungal, analgesic, antiviral, and cardiovascular drugs. Especially useful drugs include the respiratory drugs albuterol, salmeterol and amiloride, fluticasone esters, beclomethasone esters and ( − )-4-amino-3,5-dichloro-$\alpha$-[[[6-(2-pyridinyl)ethoxy]hexyl]amino]methyl]benzenemethanol.

U.S. Pat. No. 3,644,353, incorporated herein by reference, teaches a group of bronchodilating compounds that are particularly useful in the treatment of asthma and other respiratory diseases. The preferred compound taught therein is $\alpha^1$-tert-butylaminomethyl-4-hydroxy-m-xylene-$\alpha^1$, $\alpha^3$-diol, also known in the United States by its generic name, "albuterol" and, in most other countries, "salbutamol." This compound, especially in aerosol form, has been widely accepted by the medical community in the treatment of asthma.

Salmeterol, chemically named 4-hydroxy-$\alpha'$-[[[6[(4-phenylbutyl)oxy]hexyl]amino]methyl]-1,3-benzenedimethanol, disclosed in British Patent Application No. 8,310,477, is a second generation bronchodilator which is longer acting and more potent than albuterol. This compound is in not yet marketed in the United States, but clinical trials in other countries indicate that a preferred mode of administration is by way of aerosol inhalation.

The genetic disease cystic fibrosis is characterized by abnormalities that produce excessive pulmonary secretion which can make breathing difficult. U.S. Pat. No. 4,501,729, incorporated herein by reference, discloses the use of the drug amiloride in an aerosol formulation to reduce the excess secretion.

United Kingdom Patent Specification No. 2088877 discloses fluticasone esters. Fluticasone esters are corticosteriods having topical anti-inflammatory action. Corticosteroids may be used in the management of patients whose asthma is inadequately treated by bronchodilators and/or sodium cromoglycate.

A further class of corticosteroids having topical antiinflammatory action, beclomethasone esters, are described in United Kingdom Patent Specification No. 1 047 519.

( − )-4-Amino-3,5-dichloro-$\alpha$-[[[6-[2-(2-pyridinyl)ethoxy]hexyl]amino]methyl]benzenemethanol is a bronchodilator.

Where appropriate the drugs may be used in the form of salts (e.g. as alkali metal or amine salts or as acid addition salts) or as esters (e.g. as lower alkyl esters).

For use in the invention, albuterol will preferably be in the form of the sulphate salt or the free base and salmeterol will preferably be in the form of its 1-hydroxy-2-naphthoate salt. The preferred fluticasone ester for use in the invention is fluticasone propionate, and the preferred beclomethasone ester is beclomethasone dipropionate.

In addition to surfactants it may be desirable to add other excipients to an aerosol formulation to improve drug delivery, shelf life and patient acceptance. Such optional excipients include, but are not limited to, coloring agents, taste masking agents, buffers, antioxidants and chemical stabilizers.

Inhalation drugs, or a pharmaceutically acceptable salt hereof, may be micronized by, for example, conventional jet mill micronizing to particles ranging from about 0.1 to about 10.0 microns and preferably from about 0.5 to about 5.0 microns. The micronized inhalation drug or combination of drugs are mixed with one or more P 134a-soluble surfactants and, optionally, other excipients and then placed in a suitable container capable of withstanding the vapor pressure of P 134a and fitted with a metering valve. The propellant is then forced as a liquid through the valve into the container. The completed MDI is shaken vigorously to form the suspension.

Alternatively, an MDI can also be produced by adding drug, surfactant and liquefied propellant 134a (chilled below it's boiling point) to the container and then a metering valve fitted to the container. The completed MDI can then be brought to ambient temperature and shaken vigorously to form the suspension.

MDI's prepared according to the teachings herein may be used in the same way as currently marketed MDI's which use CFC's or hydrocarbon propellants. For example, in the case of albuterol, amount of drug, surfactant and propellant can be adjusted to deliver 90 $\mu$g per valve actuation, the dose delivered in currently marketed albuterol MDI's.

Particular 134a-soluble surfactants include perfluorinated surfactants, especially perfluoroalkanoic acid surfactants having greater than 4 but 20 or less carbons, preferably from 8 to 10 carbons. Also particularly suitable are a mixture of potassium perfluoroalkyl sulfonates and a mixture of ammonium perfluoroalkyl carboxylates available under the trademarks FC-95 and FC-143, respectively, from 3M Corporation, Saint Paul, Minn. Most suitable are the perfluoroalkanoic acids, perfluorooctanoic acid and perfluorodecanoic acid.

The ratio of surfactant to drug is from about 1:100 to about 1:0.5 by weight, preferably in the range of about 1:50 to about 1:1 and most preferably in the range of about 1:25 to about 1:1 by weight. The amount of P 134a can be varied according to the amount of drug formulation to be delivered with each activation of the dose metering valve. Typically for an inhalation drug the amount of P 134a for each formulation of active drug depends on the volume of the metering valve and the dose desired. However the ratio of active drug or drugs to P 134a is in the range from about 1:100 to about 1:4000 by weight. For example, for albuterol in an aerosol inhalation system outfitted with a Bespak BK300 valve, 18 g of P 134a are utilized per 50 mg of albuterol to deliver an effective dose of albuterol.

The instant invention thus provides an aerosol inhalation drug formulation comprising a physiologically effective amount of a micronized drug suitable for inhalation therapy and a propellant 134a-soluble surfactant in suspension in propellant 134a and optionally other excipients.

The following examples are presented for illustration of the invention and are not to be construed as a limitation thereto.

EXAMPLES

General Procedure

Micronized drug and surfactant (if used) are weighed into a 15 mL transparent aerosol vial (No. S-24F6, produced by Wheaton Industries, NJ). A metering valve (Bespak valve No. BK300 produced by Bespak plc, England) is crimped onto each vial. Finally, Propellant 134a (from E. I. DuPont de Nemours and Company, Wilmington Del.) is added to the vial through the valve. Vials are then vigorously shaken for 30 min with a wrist-action shaker.

Immediately after shaking, the suspension in the transparent vial is very milky or turbid. If left undisturbed, the drug particles eventually flocculate and concentrate at the gas/liquid interface (creaming) or at the bottom of the vial (settling) leaving behind a relatively clear Propellant 134a region. By shaking a formulation that has separated, it quickly re-disperses to a milky suspension. Suspension stability is assessed by monitoring the rate at which the drug particles flocculates as evidenced by the time required for the suspension to become coarse and/or to develop a relatively clear propellant region. If significant flocculation occurs, that is, a cognizable coarseness and/or clear region can be observed, in less than about 15 sec., the suspension is deemed not stable enough for a practical aerosol inhalation drug formulation.

Alternatively, several suspensions can be shaken simultaneously and the most stable suspension designated as the last one to separate. A suspension of drug in Propellant 134a with no surfactant is used as a control and reference for measuring the stability of the formulations.

The drug and propellant weight ratio is selected based on reasonable ranges of marketed products. The ratio of surfactant weight to drug weight is varied by keeping the drug weight constant and increasing the surfactant weight.

Using the procedure described above, the following data shown on Table 1 below was obtained:

TABLE 1

| | Drug (amount) | Surfactant (amount) | Approximate Time Before Significant Flocculation Observed (sec) |
|---|---|---|---|
| Control 1 | albuterol (50 mg) | none | <2 |
| Control 2 | albuterol (50 mg) | oleic acid (10 mg) | <2 |
| Control 3 | albuterol (50 mg) | perfluorobutyric acid (10 mg) | <2 |
| Example 1 | albuterol (50 mg) | perfluoroctanoic acid (5 mg) | 30 |
| Example 2 | albuterol (50 mg) | perfluoroctanoic acid (25 mg) | 30 |
| Example 3 | albuterol (50 mg) | perfluoroctanoic acid (50 mg) | 30 |
| Example 4 | albuterol (50 mg) | perfluorodecanoic acid (5 mg) | 30 |
| Example 5 | albuterol (50 mg) | perfluorodecanoic acid (25 mg) | 30 |
| Example 6 | albuterol (50 mg) | FC-143[1] (5 mg) | 30 |
| Example 7 | albuterol (50 mg) | FC-143 (50 mg) | 30 |
| Example 8 | albuterol (50 mg) | FC-95[2] (5 mg) | 30 |
| Example 9 | albuterol (50 mg) | FC-95 (50 mg) | 30 |
| Example 10 | salmeterol (20 mg) | perfluorodecanoic acid (5 mg) | 180 |
| Example 11 | salmeterol (20 mg) | perfluorodecanoic acid (50 mg) | 180 |
| Example 12 | salmeterol (10 mg) | perfluorodecanoic acid (0.5 mg) | 240 |
| Example 13 | salmeterol (10 mg) | perfluorodecanoic acid (0.1 mg) | 80 |
| Example 14 | salmeterol (10 mg) | FC-143 (1 mg) | 25 |
| Example 15 | salmeterol (10 mg) | FC-95 (1 mg) | 40 |
| Example 16 | amiloride HC1 (100 mg) | perfluorodecanoic acid (20 mg) | 150 |
| Example 17 | amiloride HC1 (100 mg) | perfluorodecanoic acid (70 mg) | 150 |

Propellant 134a weight is 18 g in each control and example.
[1]Trademark of 3M Co. for a mixture of ammonium perfluoroalkyl carboxylates
[2]Trademark of 3M Co. for a mixture of potassium perfluoroalkyl sulfonates In the case of albuterol, the rate of particle settling after flocculation tended to increase with surfactant concentration.

The following are examples of stable micronized drug suspension formulations according to the invention.

EXAMPLE 18

Chilled propellant 134a (18 g) was added to perfluorodecanoic acid (25 mg) in a glass aerosol vial. Micronised Beclomethansone dipropionate (50 mg) was added and a metering valve crimped into place. The process was performed in a dry box.

EXAMPLE 19

Chilled propellant 134a (18 g) was added to perfluorodecanoic acid (50 mg) in a glass aerosol vial. Micronised Beclomethanasone dipropionate (50 mg) was added and a metering valve crimped into place. The process was performed in a dry box.

EXAMPLE 20

Chilled propellant 134a (18 g) was added to perfluorodecanoic acid (1 mg) in a glass aerosol vial. Micronised Albuterol sulphate (32 mg) was added and a metering valve crimped into place. The process was performed in a dry box.

EXAMPLE 21

Micronised fluticasone propionate (50 mg) and perfluorodecanoic acid (20 mg) were weigh into a glass aerosol vial. A metering valve was crimped onto the vial and propellant 134a (18 g) added to the vial throught the valve.

EXAMPLE 22

Micronised fluticasone propionate (50 mg) and perfluorodecanoic acid (50 mg) were weigh into a glass aerosol vial. A metering valve was crimped onto the vial and propellant 134a (18 g) added to the vial throught the valve.

I claim:

1. An aerosol inhalation drug formulation consisting essentially of a physiologically effective amount of a micronized inhalation drug and a 1,1,1,2-tetrafluoroethane-soluble, perfluoronated surfactant in suspension in 1,1,1,2-tetrafluoroethane.

2. A formulation of claim 1 wherein the ratio of said surfactant to said drug is from about 1:100 to about 1:0.5 by weight.

3. A formulation of claim 1 wherein the ratio of said drug to 1,1,1,2-tetrafluoroethane is from about 1:100 to about 1:4000 by weight.

4. A formulation of claim 1 wherein said surfactant is a perfluoroalkanoic acid of greater than 4 carbons but not greater than 20 carbons.

5. A formulation of claim 4 wherein said perfluoroalkanonic acid is perfluorooctanoic acid or perfluorodecanoic acid.

6. A formulation of claim 1 wherein said inhalation drug is albuterol or a pharmaceutically acceptable salt thereof.

7. A formulation of claim 1 wherein said inhalation drug is salmeterol or a pharmaceutically acceptable salt thereof.

8. A formulation of claim 1 wherein said inhalation drug is amiloride or a pharmaceutically acceptable salt thereof.

9. A formulation of claim 1 wherein said 1,1,1,2-tetrafluoroethane-soluble, perfluoronated surfactant is potassium perfluoroalkyl sulfonates, ammonium perfluoroalkyl carboxylates or a combination thereof.

10. A method of improving the stability of a micronized, aerosol inhalation drug suspension in 1,1,1,2-tetrafluoroethane consisting essentially of the addition of a 1,1,1,2-tetrafluoroethane-soluble, perfluoronated surfactant to said suspension.

11. A method of claim 10 wherein said drug is selected from the group consisting of albuterol, salmeterol, amiloride, fluticasone propionate, beclomethasone dipropionate or (−)-4-amino-3,5-dichloro-α-[[[6-(2-pyridinyl)ethoxy]hexy]amino]methyl]benzenemethanol, and said surfact is a 1,1,1,2-tetrafluoroethane-soluble, -soluble perfluorinated surfactant.

12. A method of claim 11 wherein said drug is albuterol, salmeterol or amiloride and said surfactant is a 1,1,1,2-tetrafluoroethane-soluble, perfluorinated surfactants.

13. A method of claim 11 wherein said surfactant is a perfluoroalkanoic acid of greater than 4 carbons but not greater than 20 carbons.

14. A method of claim 11 wherein said surfactant is potassium perfluoroalkyl sulfonates ammonium perfluoroalky carboxylates or a combination thereof.

15. A method of claim 11 wherein said surfactant is perfluoroctanoic acid, perfluorodecanoic acid or a combination thereof and the ratio of surfactant to drug is from about 1:40 to about 1:0.5 by weight and the ratio of drug to 1,1,1,2-tetrafluoroethane is from about 1:100 to about 1:4000 by weight.

16. A method of claim 11 wherein said surfactant is potassium perfluoroalkyl sulfonates ammonium perfluoroalkyl carboxylates or a combination thereof and the ratio of surfactant to drug is from about 1:40 to about 1:0.5 by weight and the ratio of drug to 1,1,1,2-tetrafluoroethane is from about 1:100 to about 1:4000 by weight.

17. An aerosol inhalation drug formulation consisting essentially of a physiologically effective amount of micronized drug selected from the group albuterol, salmeterol and amiloride or a pharmaceutically acceptable salt thereof, a 1,1,1,2-tetrafluoroethane-soluble, perfluoronated surfactant in suspension in 1,1,1,2-tetrafluoroethane wherein the ratio of said surfactant to said drug is from about 1:100 to about 1:05 by weight and the ratio of drug to 1,1,1,2-tetrafluoroethane is from about 1:100 to about 1:4000 by weight.

18. A formulation of claim 17 wherein said 1,1,1,2-tetrafluoroethane-soluble, perfluoronated surfactant is perfluoroctanoic acid, perfluorodecanoic acid, ammonium perfluoroalkyl carboxylates or potassium perfluoroalkyl sulfonates.

19. A formulation of claim 1 wherein said inhalation drug is a fluticasone ester.

20. A formulation of claim 1 wherein said inhalation drug is a beclomethasone ester.

21. A formulation of claim 1 wherein said inhalation drug is (−)-4-amino-3,5-dichloro-a-[[[6-(2-pyridinyl)ethoxy]hexy]amino]methyl]benzenemethanol.

* * * * *